United States Patent
Tsai

(10) Patent No.: US 10,448,808 B2
(45) Date of Patent: Oct. 22, 2019

(54) DISPOSABLE MEDICAL DEVICE WITH A LIGHTING EFFECT

(71) Applicant: Yih-Chiou Tsai, Taichung (TW)

(72) Inventor: Yih-Chiou Tsai, Taichung (TW)

( * ) Notice: Subject to any disclaimer, the term of this patent is extended or adjusted under 35 U.S.C. 154(b) by 36 days.

(21) Appl. No.: 15/437,213

(22) Filed: Feb. 20, 2017

(65) Prior Publication Data

US 2018/0235444 A1   Aug. 23, 2018

(51) Int. Cl.
| | |
|---|---|
| *A61B 1/00* | (2006.01) |
| *A61B 1/31* | (2006.01) |
| *A61B 1/32* | (2006.01) |
| *A61B 1/303* | (2006.01) |
| *A61B 1/06* | (2006.01) |

(52) U.S. Cl.
CPC ........ *A61B 1/00103* (2013.01); *A61B 1/0014* (2013.01); *A61B 1/00032* (2013.01); *A61B 1/00108* (2013.01); *A61B 1/00128* (2013.01); *A61B 1/0669* (2013.01); *A61B 1/0684* (2013.01); *A61B 1/303* (2013.01); *A61B 1/31* (2013.01); *A61B 1/32* (2013.01)

(58) Field of Classification Search
CPC ... A61B 1/303; A61B 1/31; A61B 1/06–0692; A61B 1/0206
See application file for complete search history.

(56) References Cited

U.S. PATENT DOCUMENTS

| | | | |
|---|---|---|---|
| 4,300,541 A | 11/1981 | Burgin | |
| 5,165,387 A | 11/1992 | Woodson | |
| 5,394,865 A * | 3/1995 | Salerno | A61B 1/2676 600/194 |
| 5,465,709 A * | 11/1995 | Dickie | A61B 1/32 600/223 |
| 6,981,945 B1 * | 1/2006 | Sarvazyan | A61B 1/00147 600/131 |

(Continued)

FOREIGN PATENT DOCUMENTS

| | | |
|---|---|---|
| CN | 203841677 U | 9/2014 |
| WO | 2012-010857 A1 | 1/2012 |

OTHER PUBLICATIONS

Extended European Search Report for European Patent Application No. 17157111.0 dated Aug. 2, 2017 (8 pages).

*Primary Examiner* — Nicholas J Plionis
(74) *Attorney, Agent, or Firm* — Withrow & Terranova, P.L.L.C.; Vincent K. Gustafson

(57) ABSTRACT

A disposable medical device with a lighting effect has a body and a light assembly. The body has an inspection portion, a grip portion, and a placement portion. The light assembly is detachably connected to the body and has an outer casing, a lighting module, and a power supply module. The outer casing is detachably connected to the placement portion of the body, and has a chamber, a communicating hole, and a through hole. The lighting module is deposited in the outer casing and has a luminous body and a pressing-conductive arm. The pressing-conductive arm is swingably deposited in the outer casing, is selectively and electrically connected to the luminous body, and has an abutting portion and a conductive portion. The power supply module is deposited in the chamber, and is selectively and electrically connected to the lighting module and the conductive portion of the pressing-conductive arm.

19 Claims, 13 Drawing Sheets

(56) References Cited

U.S. PATENT DOCUMENTS

| | | | |
|---|---|---|---|
| 2005/0182291 A1* | 8/2005 | Hirata | A61B 1/00096 600/101 |
| 2009/0005647 A1* | 1/2009 | Bozdag | A61B 1/31 600/235 |
| 2009/0198108 A1 | 8/2009 | Chen et al. | |
| 2011/0065991 A1* | 3/2011 | Sarvazyan | A61B 1/0052 600/131 |
| 2012/0016204 A1* | 1/2012 | Bastia | A61B 1/00108 600/245 |
| 2014/0275790 A1 | 9/2014 | Vivenzio et al. | |

* cited by examiner

US 10,448,808 B2

DISPOSABLE MEDICAL DEVICE WITH A LIGHTING EFFECT

BACKGROUND OF THE INVENTION

1. Technical Field

The present invention relates to a disposable medical device, and more particularly to a disposable medical device that may provide an auxiliary lighting effect in visual inspection or treatment, may deposit a light assembly on the disposable medical device depending on need, and may reduce waste of resources and solve the environmental problems effectively.

2. Description of the Related Art

Conventional disposable medical devices include anal speculums, vaginal speculums, endoscopes or proctoscopes, etc. In the screening or treatment, the conventional disposable medical device is inserted into the patient's examination organs (such as the anus or vagina, etc.), and an appropriate light source is needed for clearly observing the status of the screening or treatment sites. A conventional folding searchlight is used to provide a lighting effect, may be partially shielded by the medical personnel in use, and cannot be completely irradiated into the internal organs of a human. In addition, the conventional folding searchlight is expensive and heavy, and a plug-in power supply is needed for the conventional folding searchlight. When patients are at remote areas far away from the medical institution, this will cause a lot of inconvenience, and the requirement of an external power supply may make the device not always readily available for use.

In view of the above-described problems, a conventional disposable medical device with a lighting effect has been designed and manufactured. Though the conventional disposable medical device may provide an auxiliary lighting effect to the user, a light assembly is directly and securely deposited on the conventional disposable medical device, the structure of the conventional disposable medical device may be complicated, and the assembly time and the manufacturing cost are increased. Additionally, whether the light assembly is needed or not for the visual screening or treatment, in either case the entire disposable medical device is required to be discarded after use under the safety and hygiene considerations, and this may cause unnecessary waste of resources and other related environmental issues.

The disposable medical device with a lighting effect in accordance with the present invention mitigates or obviates the aforementioned problems.

SUMMARY

The primary objective of the present invention is to provide a disposable medical device that may provide an auxiliary lighting effect in visual inspection or treatment, may deposit a light assembly on the disposable medical device according to a user's need conveniently, and may reduce waste of resources and solve the environmental problems effectively.

The disposable medical device with a lighting effect in accordance with the present invention has a body and a light assembly. The body has an inspection portion, a grip portion, and a placement portion. The light assembly is detachably connected to the body and has an outer casing, a lighting module, and a power supply module. The outer casing is detachably connected to the placement portion of the body, and has a chamber, a communicating hole, and a through hole. The lighting module is deposited in the outer casing and has a luminous body and a pressing-conductive arm. The pressing-conductive arm is swingably deposited in the outer casing, is selectively and electrically connected to the luminous body, and has an abutting portion and a conductive portion. The power supply module is deposited in the chamber, and is selectively and electrically connected to the lighting module and the conductive portion of the pressing-conductive arm.

Other objectives, advantages and novel features of the invention will become more apparent from the following detailed description when taken in conjunction with the accompanying drawings.

DETAILED DESCRIPTION

Figure 1:
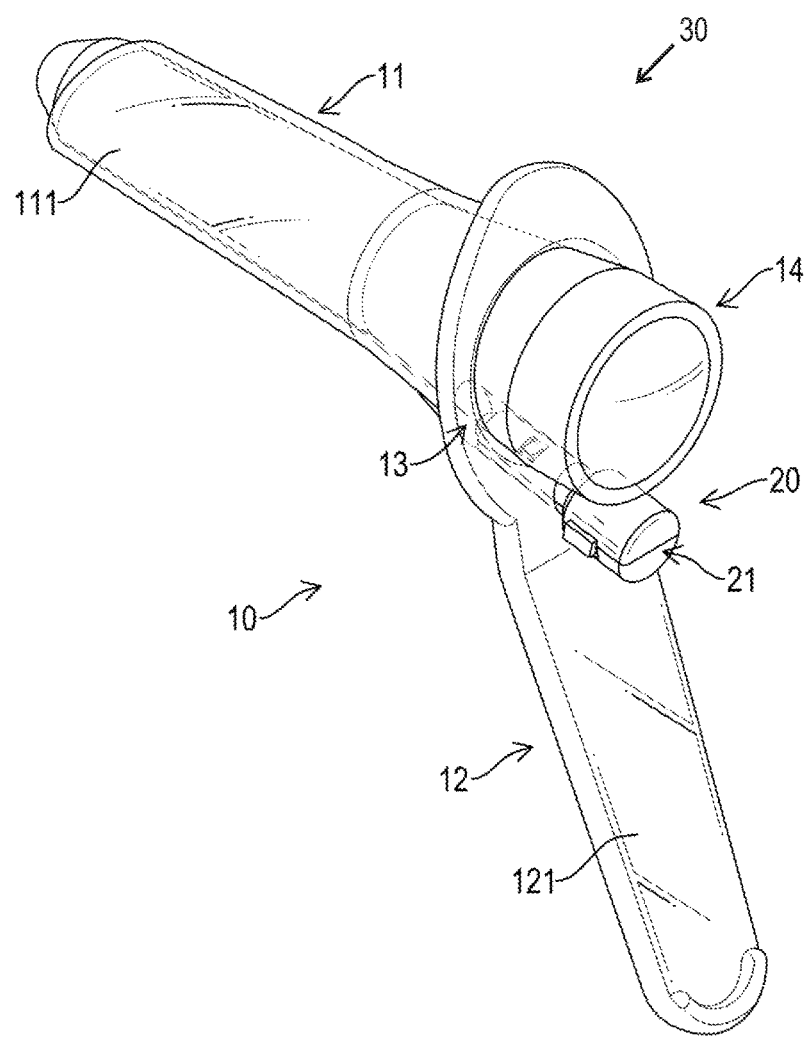
FIG. 1 is a perspective view of a first embodiment of a disposable medical device with a lighting effect in accordance with the present invention.
Figure 2:
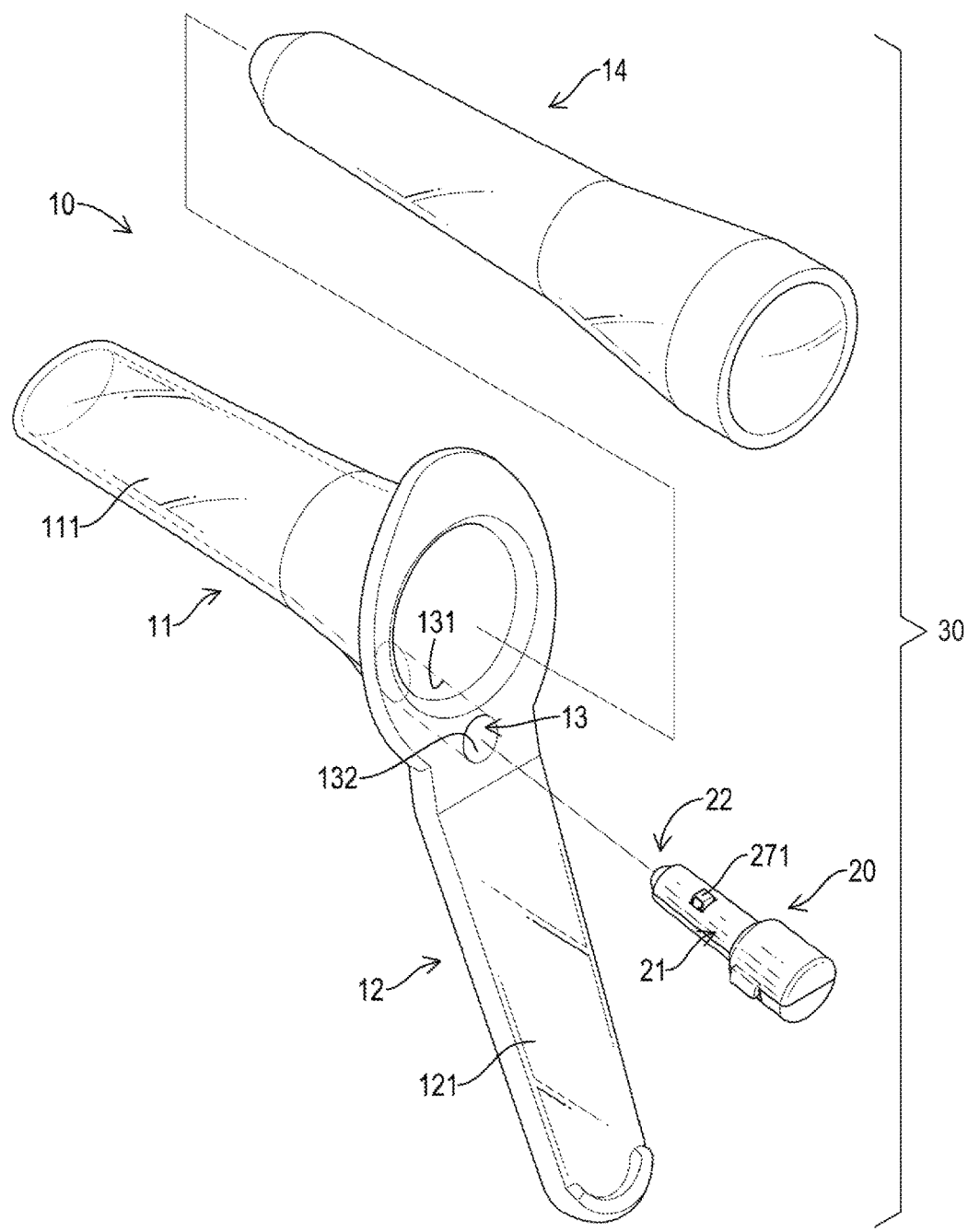
FIG. 2 is an exploded perspective view of the disposable medical device in FIG. 1.
Figure 3:
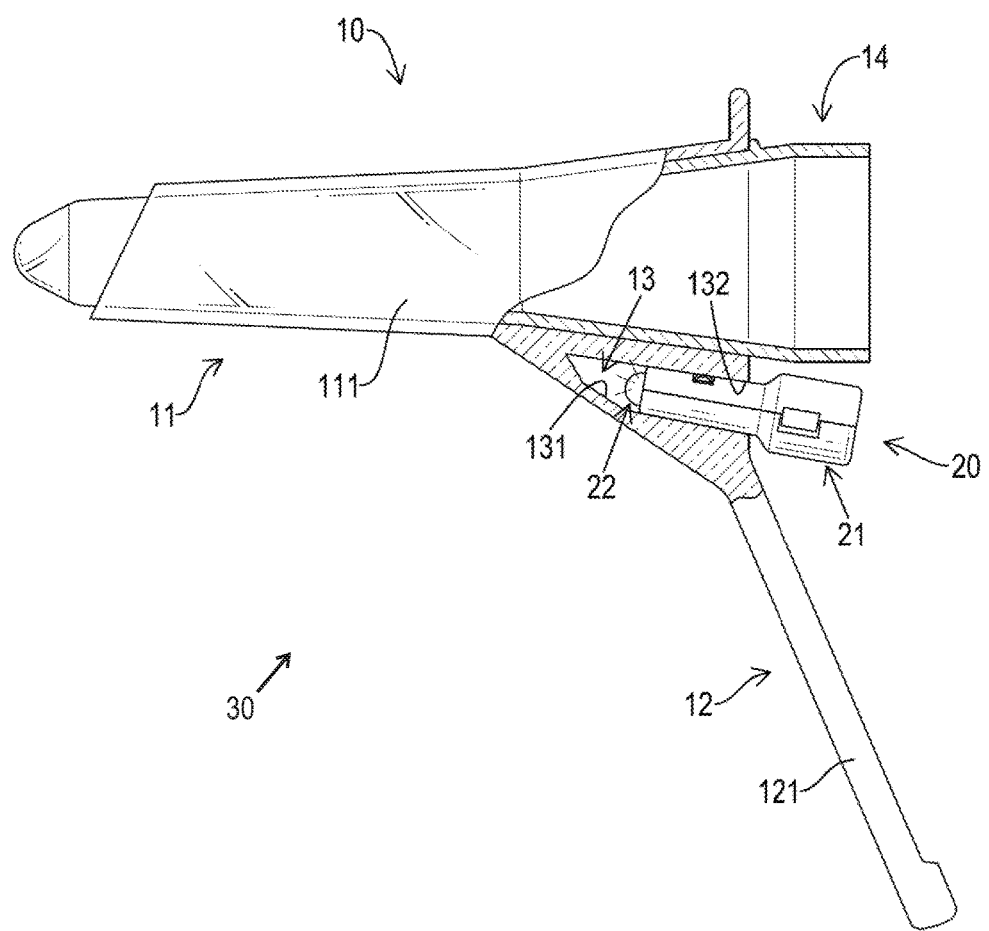
FIG. 3 is a side view in partial section of the disposable medical device in FIG. 1.

With reference to FIGS. 1 to 3, a first embodiment of a disposable medical device 30 with a lighting effect in accordance with the present invention has a body 10 and a light assembly 20.

The body 10 has an inspection portion 11, a grip portion 12, and a placement portion 13. The inspection portion 11 is used for intrusive screening or treatment of a patient's organs. The grip portion 12 is connected to the inspection portion 11 for gripping by the medical personnel such as doctors. The placement portion 13 is deposited on the body 10 and toward the inspection portion 11.

In the first embodiment of the disposable medical device 30 with a lighting effect according to the present invention, the body 10 is an anal speculum, the inspection portion 11 of the body 10 is a transparent inspection tube 111, and the grip portion 12 is a grab handle 121 connected to the inspection tube 111. The placement portion 13 is a positioning recess 131 with an opening 132 and is formed between the inspection tube 111 and the grab handle 121. Furthermore, the inspection tube 111, the grab handle 121, and the positioning recess 131 are formed as a single piece by injection molding. Additionally, the body 10 has a pushing tube 14 corresponding to and deposited in the inspection tube 111.

Figure 4:
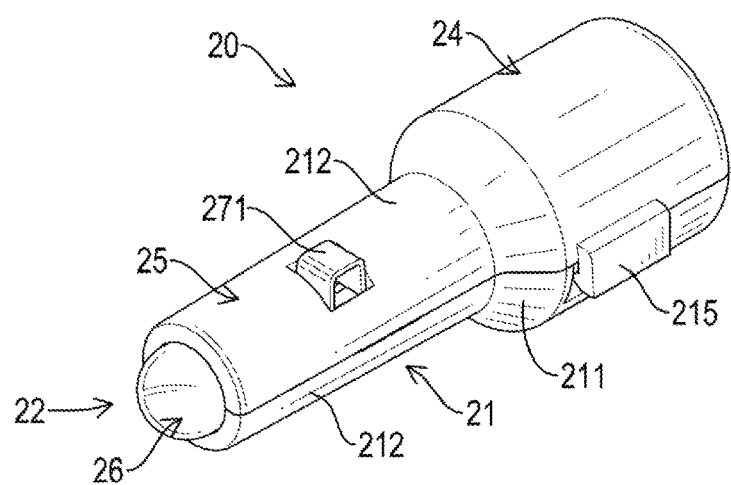
FIG. 4 is an enlarged perspective view of a light assembly of the disposable medical device in FIG. 1.
Figure 5:
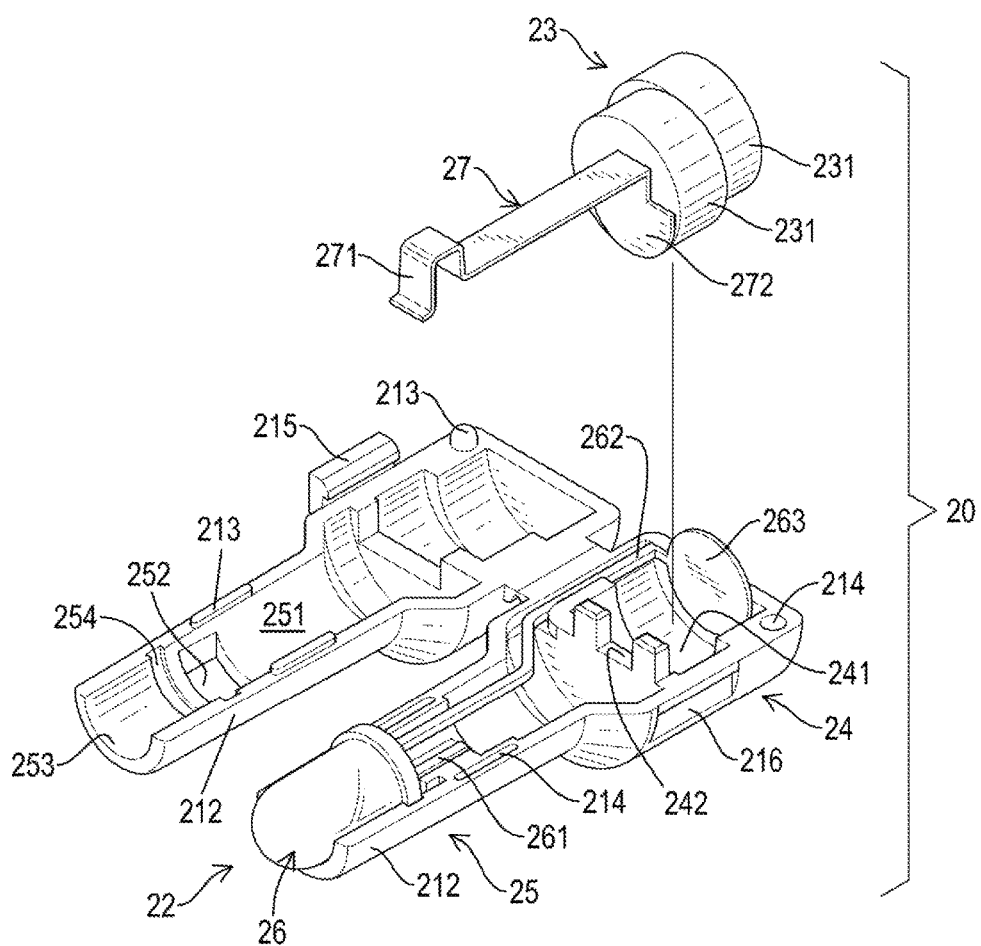
FIG. 5 is an exploded perspective view of the light assembly of the disposable medical device in FIG. 4.
Figure 6:
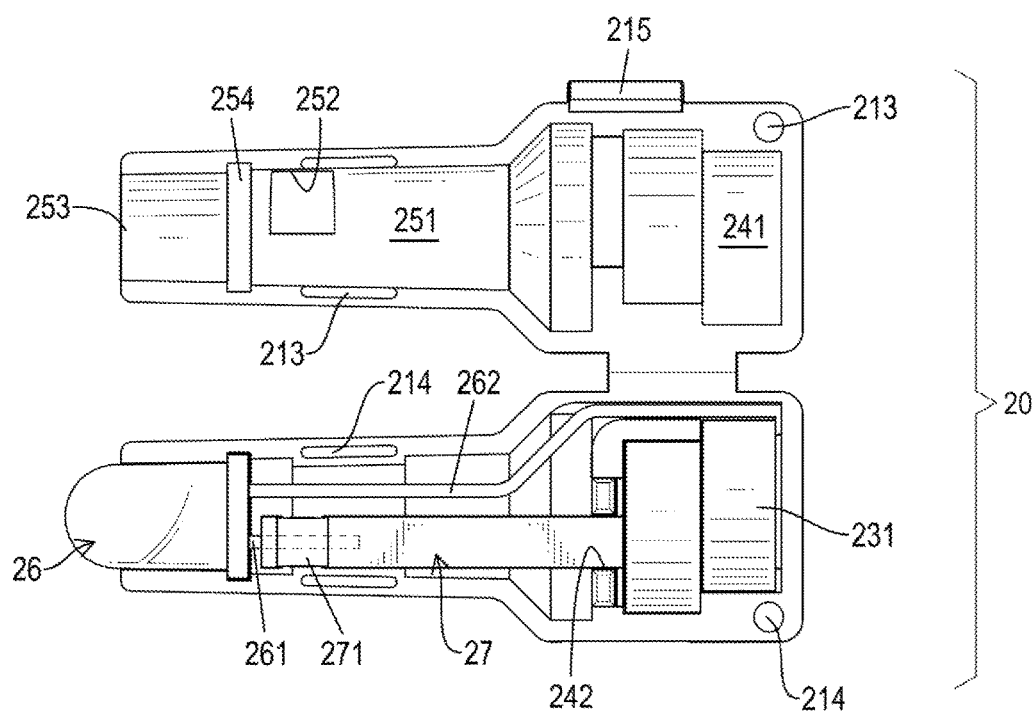
FIG. 6 is a top view of the light assembly of the disposable medical device in FIG. 4 under an unfolded condition.

With reference to FIGS. 4 to 6, the light assembly 20 is detachably connected to the body 10 and has an outer casing 21, a lighting module 22, and a power supply module 23. The outer casing 21 is a hollow shell made by plastic molding, is detachably connected to the placement portion 13 of the body 10, and has a front end extending in the positioning recess 131 of the body 10 via the opening 132 of the placement portion 13. The outer casing 21 has a base 24 and an extending seat 25. The base 24 has a chamber 241 for accommodating the power supply module 23. Furthermore, the base 24 has a through recess 242 formed at a front end of the base 24 and communicating with the chamber 241 of the base 24.

The extending seat 25 is connected to the front end of the base 24 and has an outer diameter smaller than an outer diameter of the base 24, and the outer casing 21 has two different diameters to form a stepped surface 211 between the base 24 and the extending seat 25. The extending seat 25 has a mounting recess 251, a through hole 252, and a communicating hole 253. The mounting recess 251 is formed in the extending seat 25 adjacent to the base 24 to communicate with the chamber 241 of the base 24 via the through recess 242. The through hole 252 is formed through an external surface of the extending seat 25 and communicates with the mounting recess 251. The communicating hole 253 is formed through a front end of the extending seat 25 that is opposite the base 24, and the communicating hole 253 communicates with the mounting recess 251. Additionally, the extending seat 25 has an engaging recess 254 annularly formed in an inner surface of the extending seat 25 between the through hole 252 and the communicating hole 253.

Furthermore, the base 24 and the extending seat 25 are connected to each other by injection molding, and the base 24 and the extending seat 25 are composed by two half-casings 212 that may cover each other. Each one of the half-casings 212 has a connecting side and a locking side. The two connecting sides of the two half-casings 212 are connected to each other to enable the two locking sides of the two half-casings 212 to move toward or away from each other. The outer casing 21 has multiple engaging protrusions 213 and multiple engaging holes 214 deposited on the two half-casings 212 adjacent to the two locking sides of the two half-casings 212 to enable the two half-casings 212 to form a closed structure by the engaging protrusions 213 engaging with the engaging holes 214.

Additionally, each one of the engaging protrusions 213 may be convex or elongated in shape, and each one of the engaging holes 214 has a shape corresponding to the shape of a corresponding engaging protrusion 213. Further, the outer casing 21 has a locking tab 215 and a locking recess 216 respectively deposited on the two half-casings 212 adjacent to the base 24 to enable the two half-casing 212 to connect with each other by an engagement between the locking tab 215 and the locking recess 216, and this may improve the connecting structural strength between the two half-casings 212 to prevent the two half-casings 212 from separating in use.

The lighting module 22 is deposited in the outer casing 21 and has a luminous body 26 and a pressing-conductive arm 27. The luminous body 26 is deposited in the engaging recess 254 of the extending seat 25 and has a front end extending out of the front end of the extending seat 25 via the communicating hole 253, and this enables the front end of the luminous body 26 to extend in the positioning recess 131 of the body 10 and to face the inspection tube 111. Further, the luminous body 26 may be a light-emitting diode (LED), and has a first conductive wire 261, a second conductive wire 262, and an electrode sheet 263. The first conductive wire 261 is electrically connected to the luminous body 26 and is deposited in the mounting recess 251 of the extending seat 25. The second conductive wire 262 is electrically connected to the luminous body 26 and is deposited in the chamber 241 of the base 24 via the mounting recess 251. The electrode sheet 263 is deposited in the chamber 241 of the base 24 and is electrically connected to the second conductive wire 262.

Figure 7:
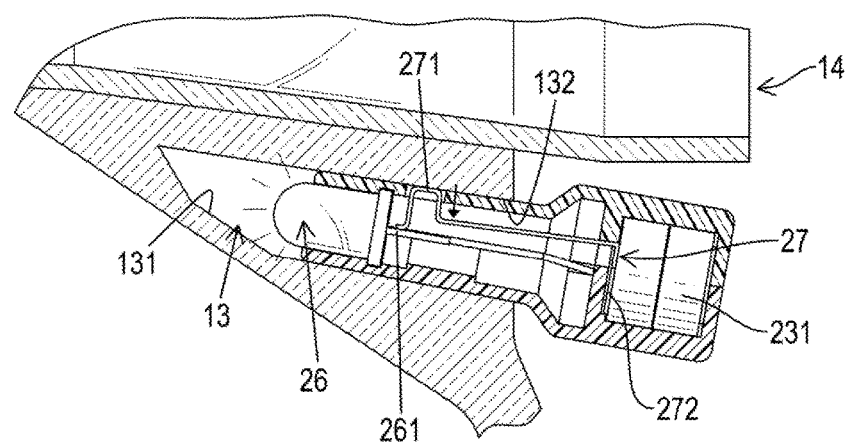
FIG. 7 is an enlarged and operational side view in partial section of the disposable medical device in FIG. 1.

The pressing-conductive arm 27 may be an elongated metal sheet, is swingably deposited in the outer casing 21, and is selectively and electrically connected to the luminous body 26. The pressing-conductive arm 27 has an outer end, an inner end, an abutting portion 271 and a conductive portion 272. The abutting portion 271 may be a curved elastic plate, is formed on the outer end of the pressing-conductive arm 27, and extends out of the outer casing 21 via the through hole 252. The abutting portion 27 has a free end deposited adjacent to the first conductive wire 261 of the luminous body 26 at a spaced interval. With reference to FIGS. 3 and 7, when the light assembly 20 is connected to the body 10 adjacent to the stepped surface 211 of the outer casing 21, the pressing-conductive arm 27 is pressed by the body 10, and this enables the free end of the abutting portion 271 to move toward and to contact the first conductive wire 261, and the two different diameters of the outer casing 21 may provide a positioning effect to user when assembling the light assembly 20 on the body 10 and may provide a firm fixing effect to the light assembly 20 when the light assembly 20 is connected with the body 10.

With further reference to FIG. 4, when the light assembly 20 is separated from the body 10, the pressing-conductive arm 27 may be restored to the original position, and this may separate the free end of the abutting portion 271 from the first conductive wire 261. The inner end of the pressing-conductive arm 27 is opposite the outer end of the pressing-conductive arm 27, and extends in the chamber 241 of the base 24 via the mounting recess 251. The conductive portion 272 may be an electrode sheet and is deposited on the inner end of the pressing-conductive arm 27.

The power supply module 23 is deposited in the outer casing 21, is selectively and electrically connected to the lighting module 22, and has multiple mercury batteries 231 stacked with each other in the chamber 241 of the base 24. The batteries 231 are electrically connected to the luminous body 26 via the electrode sheet 263, the second conductive wire 262, the conductive portion 272 and the abutting portion 271 of the pressing-conductive arm 27, and the first conductive wire 261 when the pressing-conductive arm 27 presses against the first conductive wire 261.

When the first embodiment of the disposable medical device 30 with a lighting effect is in use, with reference to FIGS. 3, 4, and 7, an end of the light assembly 20 that has the luminous body 26 mounted thereon is pushed in the positioning recess 131 via the opening 132 of the placement portion 13. When the light assembly 20 is moved relative to the body 10, the abutting portion 271 of the pressing-conductive arm 27 that extends out of the outer casing 21 via the through hole 252 may move toward the first conductive wire 261 when the outer casing 21 is moved relative to the positioning recess 131. When the free end of the abutting portion 271 abuts against the first conductive wire 261, an electrical conduction is formed among the first conductive wire 261 of the luminous body 26, the abutting portion 271 and the conductive portion 272 of the pressing-conductive arm 27, the batteries 231, and the second conductive wire 262. Then, the power required for the luminous body 26 to emit light can be provided by the batteries 231.

When the luminous body 26 emits the light, the medical personnel may grab the grab handle 121 and insert the inspection tube 11 and the pushing tube 14 into a patient's anus to stretch an inner wall of the patient's anus and to observe the internal status of the patient's anus. The light of the luminous body 26 may provide an auxiliary lighting effect to the medical personnel during the inspection.

Figure 8:
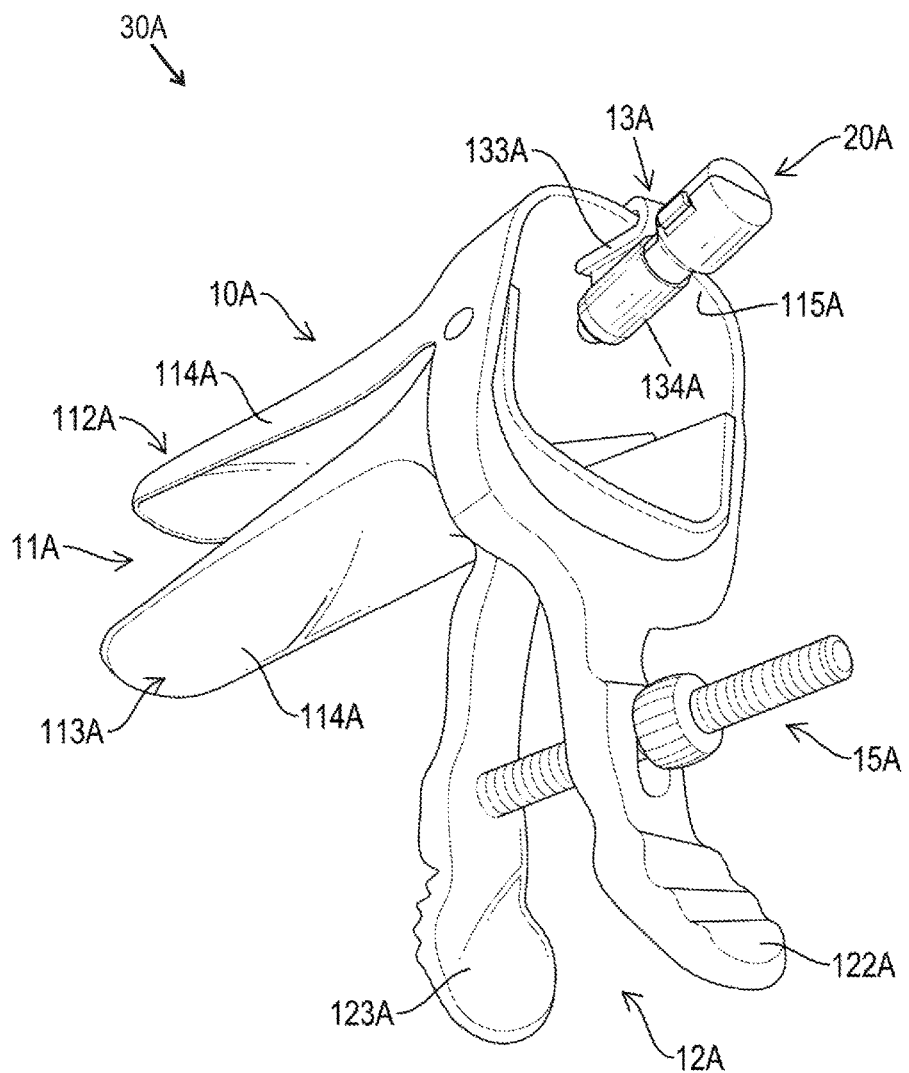
FIG. 8 is a perspective view of a second embodiment of a disposable medical device with a lighting effect in accordance with the present invention.
Figure 9:
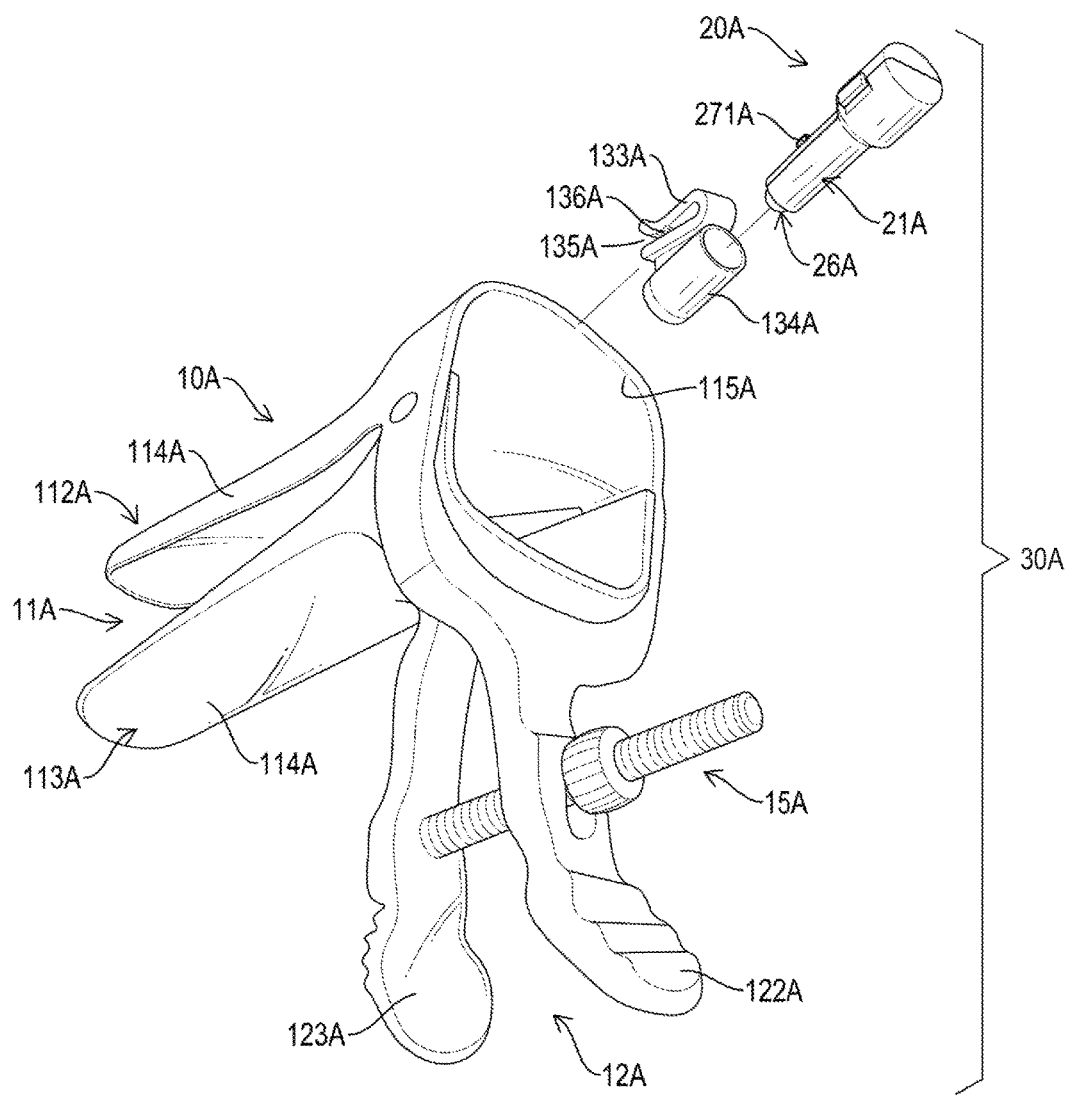
FIG. 9 is an exploded perspective view of the disposable medical device in FIG. 8.
Figure 10:
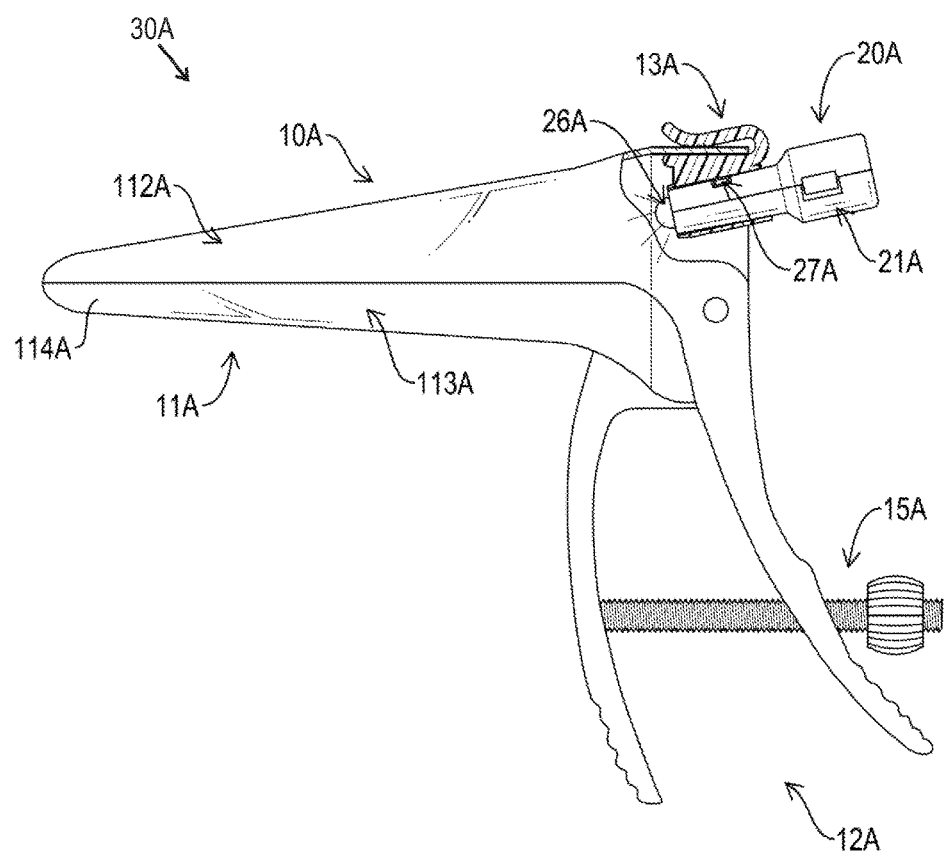
FIG. 10 is an enlarged and operational side view in partial section of the disposable medical device in FIG. 8.

With reference to FIGS. 8 to 10, a second embodiment of a disposable medical device 30A with a lighting effect in accordance with the present invention is substantially the same as the first embodiment of the disposable medical device 30 as shown in FIGS. 1 to 3 except for the following features. The body 10A is a vaginal speculum, and the inspection portion 11A of the body 10A has an upper jaw 112A and a lower jaw 113A. The lower jaw 113A is pivotally connected to the upper jaw 112A, and each one of the upper jaw 112A and the lower jaw 113A has a tongue segment 114A. The tongue segments 114A of the upper jaw 112A and the lower jaw 113A may move toward or away from each other to change an angle between the upper jaw 112A and the lower jaw 113A. Furthermore, the inspection portion 11A has a window 115A formed at rear ends of the upper jaw 112A and the lower jaw 113A.

The grip portion 12A has two operating stems 122A, 123A respectively connected to and controlling the movements of the upper jaw 112A and the lower jaw 113A. In addition, the body 10A has an adjusting structure 15A deposited between the operating stems 122A, 123A to drive and control the movements of the tongue segments 114A of the upper jaw 112A and the lower jaw 113A.

The placement portion 13A may be a fixture, is detachably connected to the upper jaw 112A or the lower jaw 113A to extend in the window 115A, and has a clamping body 133A and a mounting sleeve 134A. The clamping body 133A is connected to the rear end of the upper jaw 112A or the rear end of the lower jaw 113A, and has a clamping mouth 135A and multiple engaging teeth 136A. The clamping mouth 135A is a slit and has an inner surface, and the engaging teeth 136A are formed on and protrude from the inner surface of the clamping mouth 135A to increase the engaging and positioning effect between the clamping body 133A and one of the upper and lower jaws 112A, 113A.

Furthermore, the clamping body 133A is connected to the rear end of the upper jaw 112A, and the mounting sleeve 134A may be a hollow tube, is connected to the clamping body 133A, and extends in the window 115A. The outer casing 21A of the light assembly 20A is mounted in the mounting sleeve 134A to make the luminous body 26A toward the inspection portion 11A. With further reference to FIG. 10, when the outer casing 21A is connected to the mounting sleeve 134A, the abutting portion 271A of the pressing-conductive arm 27A is pressed by the mounting sleeve 134A and abuts the luminous body 26A to form the electrical conduction.

When the second embodiment of the disposable medical device 30A with a lighting effect is in use, with reference to FIGS. 8 to 10, the medical personnel may deposit the clamping body 133A on one of the upper and lower jaws 112A, 113A, and then insert the outer casing 21A of the light assembly 20A in the mounting sleeve 134A to connect the light assembly 20A with the body 10A. In addition, the medical personnel also can connect the outer casing 21A of the light assembly 20A with the mounting sleeve 134A firstly, and deposit the clamping body 133A on one of the upper and lower jaws 112A, 113A. As the outer casing 21A moves relative to the mounting sleeve 134A, the abutting portion 271A of the pressing-conductive arm 27A that extends out of the outer casing 21A may move close to and abut the luminous body 26A by the movement of the outer casing 21A relative to the mounting sleeve 134A, and this may enable the luminous body 26A to emit light.

With reference to FIG. 10, the tongue segments 114A of the upper and lower jaws 112A, 113A abut each other and are inserted into a patient's vagina, and the medical personnel may control the opening status between the tongue segments 114A of the upper and lower jaws 112A, 113A by operating the operating stems 122A, 123A to stretch an inner wall of the patient's vagina and to observe the internal status of the patient's vagina or the cervix. Additionally, the angle between the tongue segments 114A under the opening status can be held by the adjusting structure 15A, and the medical personnel may inspect with an auxiliary lighting effect that is provided by the luminous body 26A.

Figure 11:
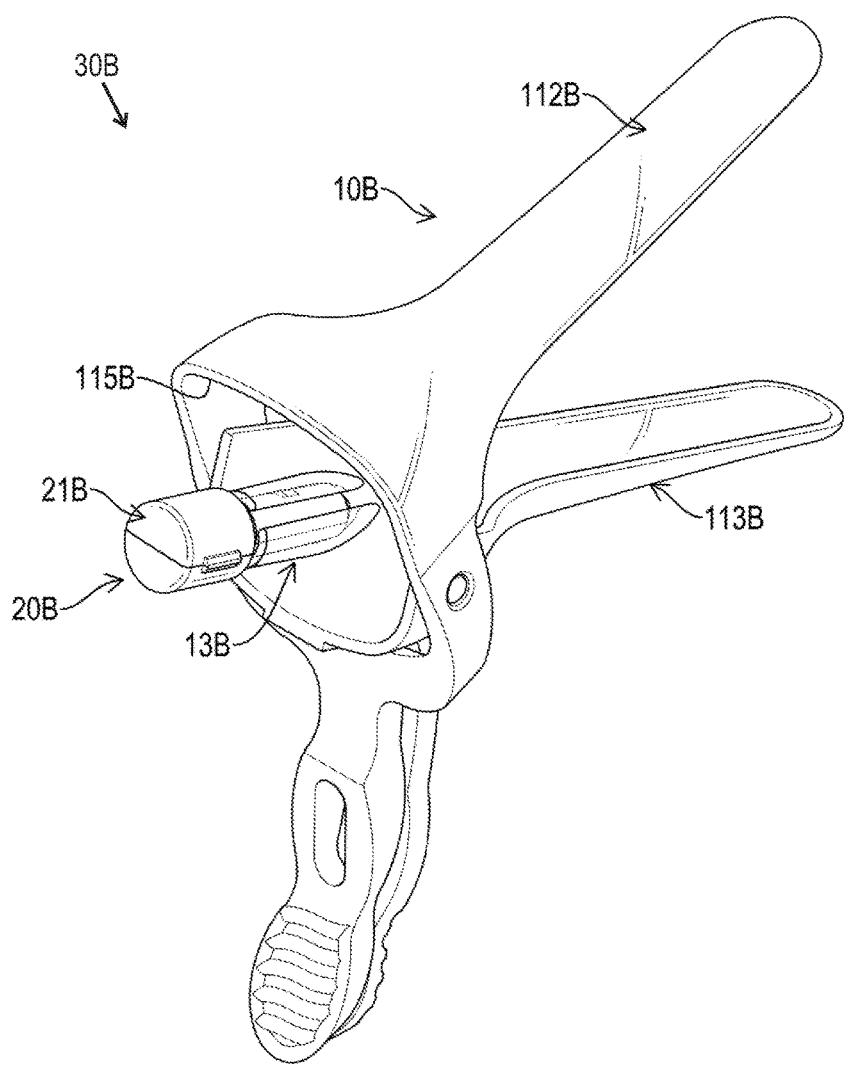
FIG. 11 is a perspective view of a third embodiment of a disposable medical device with a lighting effect in accordance with the present invention.
Figure 12:
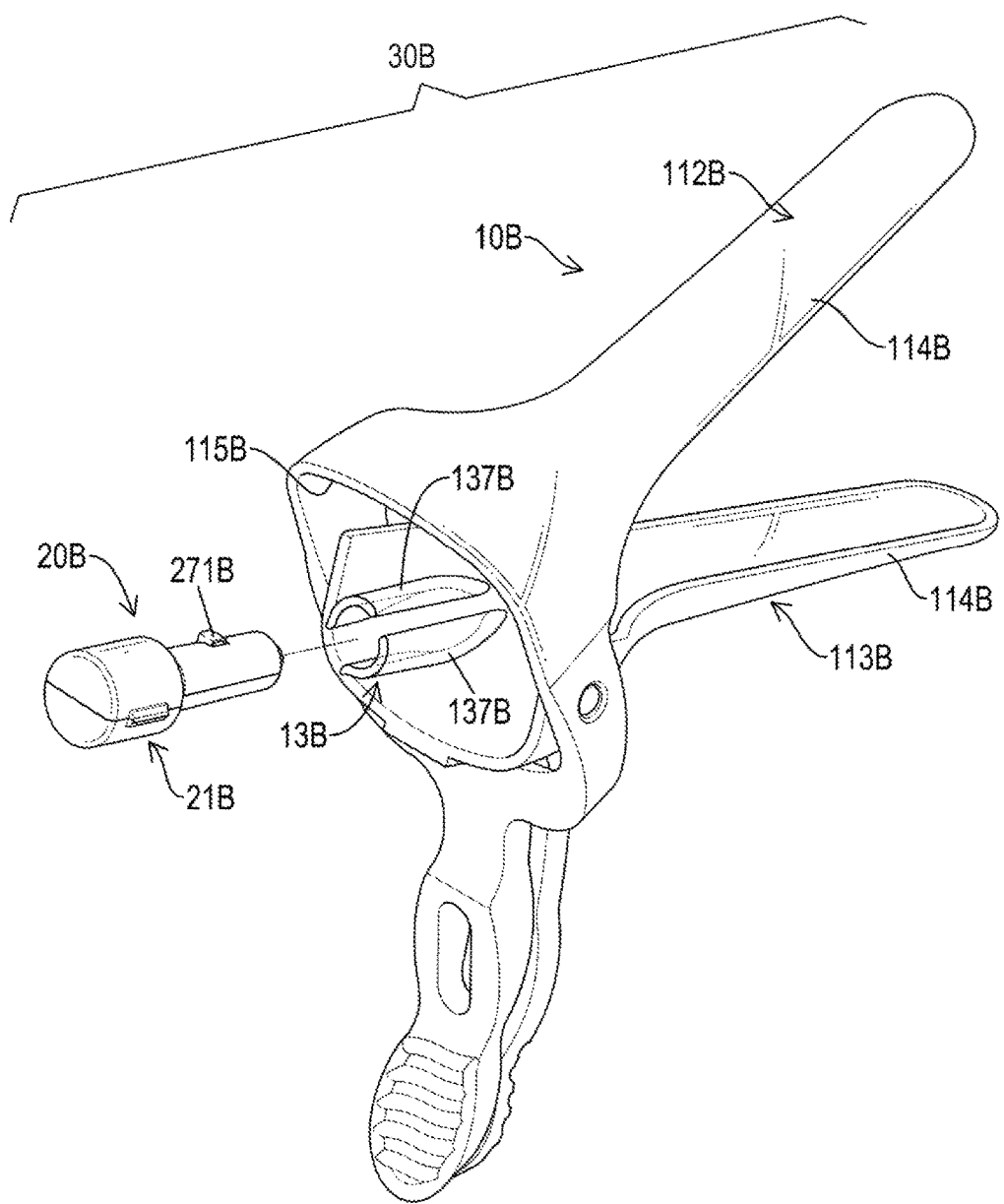
FIG. 12 is an exploded perspective view of the disposable medical device in FIG. 11.
Figure 13:
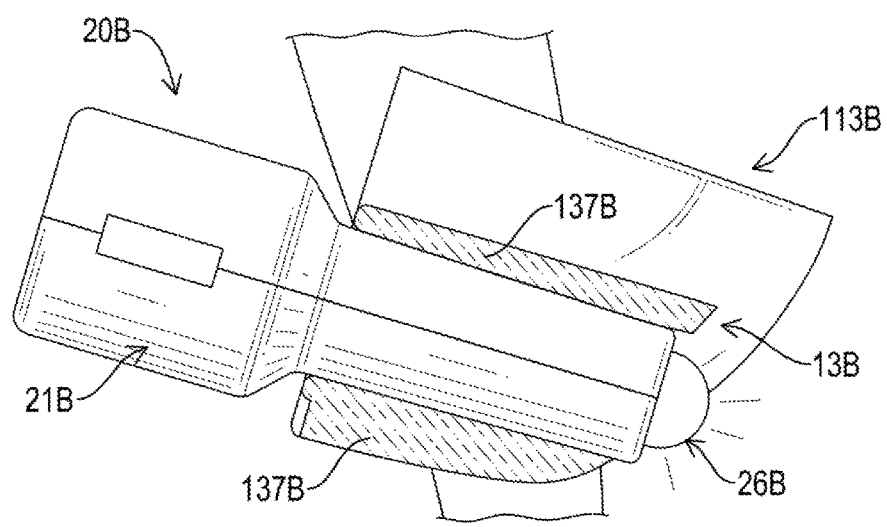
FIG. 13 is an enlarged and operational side view in partial section of the disposable medical device in FIG. 11.

With reference to FIGS. 11 to 13, a third embodiment of a disposable medical device 30B with a lighting effect in accordance with the present invention is substantially the same as the disposable medical device 30A with a lighting effect of the second embodiment as shown in FIGS. 8 to 10 except for the following features. The placement portion 13B is formed on an inner surface of one of the upper jaw 112B and the lower jaw 113B as a single piece adjacent to the rear end of said jaw 112B, 113B, and the placement portion 13B is a hollow pipe and has a front opening and a rear opening. The front opening of the placement portion 13B is deposited in a space that is formed by the upper jaw 112B and the lower jaw 113B, and the rear opening of the placement portion 13B is deposited between the upper and lower jaws 112B, 113B adjacent to the window 115B.

Further, the placement portion 13B has two curved panels 137B facing to each other at a spaced interval to form the hollow pipe, and each one of the curved panels 137B has an extending direction same as the extending directions of the tongue segments 114B of the upper and lower jaws 112B, 113B. Additionally, the placement portion 13B is formed on and protrudes from the inner surface of the lower jaw 113B as a single piece adjacent to the rear end of the lower jaw 113B, and the outer casing 21B of the light assembly 20B engages with the curved panels 137B to make the luminous body 26B toward the upper and lower jaws 112B, 113B.

When the third embodiment of the disposable medical device 30B with a lighting effect is in use, with reference to FIGS. 11 to 13, the end of the light assembly 20B that has the luminous body 26B deposited thereon is mounted between the curved panels 137B via the rear opening of the placement portion 13B. As the outer casing 21B moves relative to the curved panels 137B, the abutting portion 271B of the pressing-conductive arm 27B that extends out of the outer casing 21B may move toward and abut the luminous body 26B to enable the luminous body 26B to emit light under the electrical conduction. The upper and lower jaws 112B, 113B are inserted into the patient's vagina to stretch the inner wall of the patient's vagina and to observe the internal status of the patient's vagina or the cervix.

According to the above-mentioned structural relationships and features of the embodiments in accordance with the present invention, the through hole 252 is formed through the outer casing 21, 21A, 21B to enable the abutting portion 271, 271A, 271B of the pressing-conductive arm 27, 27A to extend out of the outer casing 21, 21A, 21B. When the light assembly 20, 20A, 20B is connected to the placement portion 13, 13A, 13B of the body 10, 10A, 10B, the abutting portion 271, 271A, 271B of the pressing-conductive arm 27, 27A is pressed to move into the outer casing 21, 21A, 21B to abut against the first conductive wire 261 of the luminous body 26, 26A, 26B. Then, the electrical conduction is formed among the first conductive wire 261 of the luminous body 26, 26A, 26B, the abutting portion 271, 271A, 271B and the conductive portion 272 of the pressing-conductive arm 27, 27A, the batteries 231, and the second conductive wire 262. Then, the power required for the luminous body 26, 26A, 26B to emit light can be provided by the batteries 231.

Furthermore, the light assembly 20, 20A, 20B is detachably connected to the body 10, 10A, 10B, and this makes the light assembly 20, 20A, 20B applicable to disposable medical devices of different types or sizes, such as anal speculums or vaginal speculums, by directly depositing the light assembly 20, 20A, 20B on the disposable medical devices conveniently and easily. Then, the medical personnel may deposit the light assembly 20, 20A, 20B on the body 10, 10A, 10B of the disposable medical device depending on need to provide an auxiliary lighting effect in visual inspection or treatment, and may reduce waste of resources and solve the environmental problems effectively.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A disposable medical device with a lighting effect comprising:
   a body having
      an inspection portion being elongated and having a front end and a rear end opposite the front end of the inspection portion;
      a grip portion connected to the rear end of the inspection portion and extending away from the inspection portion; and
      a placement portion deposited on the inspection portion of the body as a single piece adjacent to the rear end of the inspection portion, facing toward the inspection portion, and having
         a front opening;
         a rear opening communicating with the front opening; and
         two curved panels facing to each other at a spaced interval between the front opening and the rear opening to form a hollow pipe, and each one of the curved panels having an extending direction same as an extending direction of the inspection portion; and
   a light assembly detachably engaging with the curved panels of the body and having
      an outer casing detachably connected to the placement portion of the body, and having
         two ends;
         two different diameters to form a stepped surface;
         a chamber formed in the outer casing at one of the ends of the outer casing;
         a communicating hole formed through the outer casing adjacent to the other one of the two ends of the outer casing, and being opposite the chamber; and
         a through hole formed through the outer casing between the chamber and the communicating hole;
      a lighting module deposited in the outer casing and having
         a luminous body deposited in the outer casing and having a front end extending in the placement portion via the communicating hole and facing the inspection portion; and
         a pressing-conductive arm swingably deposited in the outer casing, selectively and electrically connected to the luminous body, and having
            an outer end;
            an inner end;
            an abutting portion being a curved elastic plate, formed on the outer end of the pressing-conductive arm, extending out of the outer casing via the through hole, and having a free end deposited adjacent to the luminous body at a spaced interval; and
            a conductive portion being a plate and deposited on the inner end of the pressing-conductive arm; and
      a power supply module deposited in the chamber of the outer casing, and selectively and electrically connected to the lighting module and the conductive portion of the pressing-conductive arm;
   wherein the light assembly is connected to the body adjacent to the stepped surface of the outer casing that is positioned and fixed by the two different diameters of the outer casing, the pressing-conductive arm is pressed by the body to enable the free end of the abutting portion to move toward and to contact the luminous body, and the power supply module provides power to the luminous body via the pressing-conductive arm, and the luminous body extends out of the front opening of the placement portion via the rear opening of the placement portion.

2. The disposable medical device as claimed in claim 1, wherein
   the outer casing has a base and an extending seat;
   the chamber of the outer casing is formed in the base;
   the base has a through recess formed at a front end of the base and communicating with the chamber;
   the extending seat is connected to the front end of the base, and has a mounting recess formed in the extending seat adjacent to the base and communicating with the chamber via the through recess;
   the through hole is formed through the extending seat and communicates with the mounting recess;
   the communicating hole is formed through a front end of the extending seat that is opposite the base, and communicates with the mounting recess; and
   the luminous body has
      a first conductive wire electrically connected to the luminous body and deposited in the mounting recess of the extending seat;
      a second conductive wire electrically connected to the luminous body and deposited in the chamber of the base via the mounting recess; and
      an electrode sheet deposited in the chamber of the base and electrically connected to the second conductive wire.

3. The disposable medical device as claimed in claim 2, wherein the power supply module has multiple mercury batteries stacked with each other in the chamber of the base, the batteries electrically connected to the luminous body via the electrode sheet, the second conductive wire, the conductive portion and the abutting portion of the pressing-conductive arm, and the first conductive wire when the pressing-conductive arm presses against the first conductive wire.

4. The disposable medical device as claimed in claim 3, wherein
the base and the extending seat are connected to each other by injection molding, and are composed by two half-casings;
each one of the two half-casings has
a locking side; and
a connecting side, the two connecting sides of the two half-casings connected to each other to enable the two locking sides of the two half-casings to move toward or away from each other; and
the outer casing has multiple engaging protrusions and multiple engaging holes deposited on the two half-casings adjacent to the two locking sides of the two half-casings to enable the two half-casings to form a closed structure by the engaging protrusions engaging with the engaging holes.

5. The disposable medical device as claimed in claim 4, wherein the outer casing has a locking tab and a locking recess respectively deposited on the two half-casings adjacent to the base to enable the two half-casings to connect with each other by an engagement between the locking tab and the locking recess.

6. The disposable medical device as claimed in claim 5, wherein
the extending seat has an engaging recess annularly formed in an inner surface of the extending seat between the through hole and the communicating hole; and
the luminous body is deposited in the engaging recess of the extending seat.

7. The disposable medical device as claimed in claim 6, wherein
the extending seat has an outer diameter smaller than an outer diameter of the base; and
the stepped surface of the outer casing is deposited between the base and the extending seat.

8. The disposable medical device as claimed in claim 7, wherein
the body is an anal speculum;
the inspection portion of the body is a transparent inspection tube; and
the grip portion is a grab handle and is connected to the inspection tube.

9. The disposable medical device as claimed in claim 7, wherein
the body is a vaginal speculum;
the inspection portion of the body has
an upper jaw having a tongue segment;
a lower jaw pivotally connected to the upper jaw and having a tongue segment moveable toward or away from the tongue segment of the upper jaw; and
a window formed at rear ends of the upper jaw and the lower jaw; and
the grip portion has two operating stems respectively connected to and controlling the movements of the upper jaw and the lower jaw.

10. The disposable medical device as claimed in claim 9, wherein
the placement portion is formed on an inner surface of one of the upper jaw and the lower jaw adjacent to the rear end of said jaw;
the front opening is deposited in a space that is formed by the upper jaw and the lower jaw; and
the rear opening is deposited between the upper and lower jaws adjacent to the window.

11. The disposable medical device as claimed in claim 3, wherein
the body is an anal speculum;
the inspection portion of the body is a transparent inspection tube; and
the grip portion is a grab handle and is connected to the inspection tube.

12. The disposable medical device as claimed in claim 3, wherein
the body is a vaginal speculum;
the inspection portion of the body has
an upper jaw having a tongue segment;
a lower jaw pivotally connected to the upper jaw and having a tongue segment moveable toward or away from the tongue segment of the upper jaw; and
a window formed at rear ends of the upper jaw and the lower jaw; and
the grip portion has two operating stems respectively connected to and controlling the movements of the upper jaw and the lower jaw.

13. The disposable medical device as claimed in claim 12, wherein
the placement portion is formed on an inner surface of one of the upper jaw and the lower jaw adjacent to the rear end of said jaw;
the front opening is deposited in a space that is formed by the upper jaw and the lower jaw; and
the rear opening is deposited between the upper and lower jaws adjacent to the window.

14. The disposable medical device as claimed in claim 2, wherein
the body is an anal speculum;
the inspection portion of the body is a transparent inspection tube; and
the grip portion is a grab handle and is connected to the inspection tube.

15. The disposable medical device as claimed in claim 2, wherein
the body is a vaginal speculum;
the inspection portion of the body has
an upper jaw having a tongue segment;
a lower jaw pivotally connected to the upper jaw and having a tongue segment moveable toward or away from the tongue segment of the upper jaw; and
a window formed at rear ends of the upper jaw and the lower jaw; and
the grip portion has two operating stems respectively connected to and controlling the movements of the upper jaw and the lower jaw.

16. The disposable medical device as claimed in claim 15, wherein
the placement portion is formed on an inner surface of one of the upper jaw and the lower jaw adjacent to the rear end of said jaw;
the front opening is deposited in a space that is formed by the upper jaw and the lower jaw; and
the rear opening is deposited between the upper and lower jaws adjacent to the window.

17. The disposable medical device as claimed in claim 1, wherein the body is an anal speculum;
the inspection portion of the body is a transparent inspection tube; and
the grip portion is a grab handle and is connected to the inspection tube.

18. The disposable medical device as claimed in claim 1, wherein
the body is a vaginal speculum;
the inspection portion of the body has
an upper jaw having a tongue segment;
a lower jaw pivotally connected to the upper jaw and having a tongue segment moveable toward or away from the tongue segment of the upper jaw; and
a window formed at rear ends of the upper jaw and the lower jaw; and
the grip portion has two operating stems respectively connected to and controlling the movements of the upper jaw and the lower jaw.

19. The disposable medical device as claimed in claim 18, wherein
the placement portion is formed on an inner surface of one of the upper jaw and the lower jaw adjacent to the rear end of said jaw;
the front opening is deposited in a space that is formed by the upper jaw and the lower jaw; and
the rear opening is deposited between the upper and lower jaws adjacent to the window.

* * * * *